United States Patent [19]

Fuchs et al.

[11] 3,978,105

[45] Aug. 31, 1976

[54] MANUFACTURE OF ORGANIC ISOCYANATES

[75] Inventors: Werner Fuchs, Ludwigshafen; Rolf Platz, Mannheim; Volker Vogt, Ludwigshafen, all of Germany

[73] Assignee: BASF Aktiengesellschaft, Ludwigshafen (Rhine), Germany

[22] Filed: Jan. 23, 1975

[21] Appl. No.: 543,244

[30] Foreign Application Priority Data

Feb. 1, 1974 Germany............................ 2404773

[52] U.S. Cl.......................................... 260/453 PH
[51] Int. Cl.².................................... C07C 118/02
[58] Field of Search............................. 260/453 PH

[56] References Cited

UNITED STATES PATENTS

| | | | |
|---|---|---|---|
| 2,642,449 | 6/1953 | Morningstar et al. | 260/453 |
| 2,875,225 | 2/1959 | Bohme et al. | 260/453 |

*Primary Examiner*—Lewis Gotts
*Assistant Examiner*—Dolph H. Torrence
*Attorney, Agent, or Firm*—Johnston, Keil, Thompson & Shurtleff

[57] ABSTRACT

Organic monoisocyanates and/or polyisocyanates are manufactured by reaction of primary organic amines with phosgene in the absence of organic solvents.

5 Claims, No Drawings

MANUFACTURE OF ORGANIC ISOCYANATES

This application discloses and claims subject matter described in German Patent Application No. P 24 04 773.2, filed Feb. 1, 1974, which is incorporated herein by reference.

The invention relates to a process for the manufacture of organic monoisocyanates, diisocyanates and/or polyisocyanates from phosgene and primary amines wherein the starting materials are mixed in the absence of a solvent and at the same time ground to an average particle size of from 1 to 100 $\mu$, and the resulting suspension of carbamyl chloride and amine hydrochloride in phosgene is converted to the corresponding isocyanates.

The manufacture of organic isocyanates by reacting phosgene with organic compounds containing primary amino groups, in the presence of inert diluents, at elevated temperatures and under superatmospheric pressure, is known. An essential disadvantage of this process is that isolating the isocyanates entails removing large quantities of solvents. Furthermore, almost all solvents form at least small amounts of by-products under the phosgenation reaction conditions and these by-products interfere with the course of the reaction, hinder the purification of the isocyanates and, because they entail losses of solvent, add to the cost of the manufacturing process and constitute a hazard to the environment.

Another proposal for the manufacture of isocyanates is to react primary amines with phosgene in the liquid phase at temperatures above 180°C and under high pressures. The disadvantage of this process is that the yields of isocyanates are poor when hot gaseous phosgene is reacted with hot liquid amine in the absence of a solvent. Eg., the yield of phenylisocyanate is 95% if the reaction is carried out in the presence of solvents and drops to 65% in the absence of solvents.

It is also known to manufacture polyisocyanates by two-stage processes. In the first stage of the reaction, the primary amine is mixed with excess phosgene in a closed reactor at from 10° to 30°C; the reaction mixture is then converted to polyisocyanates in a second stage at temperatures of from 100° to 200°C and higher pressure, whilst continuously removing the hydrogen chloride generated from the reaction mixture. If polyisocyanates are manufactured analogously to this process by mixing the starting materials with a conventional stirrer at temperatures below 30°C and in the absence of a solvent, the products are obtained in yields which are to be regarded as poor for industrial processes, since the solid amine, which is insoluble in phosgene, immediately forms, on the surface, a carbamyl chloride which is also insoluble in liquid phosgene, together with the amine hydrochloride. However, below the solid surface there is still some free amine which reacts with carbamyl chloride especially at high temperatures, to give urea.

It is an object of the present invention to manufacture organic isocyanates in high yields from primary amines and phosgene in the absence of solvents.

We have found that isocyanates are obtained in high yields from organic primary amines and phosgene by a process wherein the primary amines are mixed with not less than 3 moles of phosgene per amino group in the absence of an organic solvent, the reaction mixture is at the same time ground to an average particle size of from 1 to 100 $\mu$, and the resulting suspension of carbamyl chloride and amine hydrochloride in phosgene is converted to the corresponding isocyanates at temperatures of from 100° to 180°C and pressures of from 14 to 55 bars.

Numerous araliphatic, cycloaliphatic and, preferably, aliphatic and aromatic compounds, which contain at least one primary amino group in the molecule, can be used for the manufacture of the isocyanates, but preferably the industrially important diamines and polyamines are used. The following may be mentioned as specific examples: cycloaliphatic monoamines of 5 to 12, preferably of 5 to 8, carbon atoms in the cycloalkyl radical, such as cyclohexylamine and cyclooctylamine and preferably cycloaliphatic diamines of 6 to 13 carbon atoms, such as cyclohexylenediamine, 4,4'-, 4,2'- and 2,2'-diaminodicyclohexylmethane; aliphatic monoamines of 1 to 12, preferably of 1 to 6 carbon atoms, such as methylamine, ethylamine, butylamine, hexylamine, octylamine, decylamine and dodecylamine, and preferably aliphatic diamines of 2 to 6 carbon atoms, such as 1,2-diaminoethane, 1,4-diaminobutane and, preferably, 1,6-diaminohexane; aromatic monoamines of 6 to 18 carbon atoms, such as aniline, benzylamine, toluidine and naphthylamine and preferably aromatic diamines of 6 to 15 carbon atoms, such as phenylenediamine, naphthylenediamine, fluorenediamine, diphenyldiamine, anthracenediamine and, preferably, 2,4- and 2,6-toluylenediamine and 4,4'-, 2,4'- and 2,2'-diaminodiphenylmethane, and aromatic polyamines such as 2,4,6-triaminotoluene, mixtures of polyphenyl-polymethylene-polyamines, and mixtures of diaminodiphenylmethanes and polyphenyl-polymethylene-polyamines. Individual monoamines, diamines and polyamines, or mixtures thereof, may be phosgenated. Instead of the free amines, the salts of the amines with volatile acids, for example their hydrochlorides, or mixtures of the free amines and their salts with volatile acids can be employed. Since hydrogen chloride is formed as a volatile by-product of the reaction of phosgene with the primary amino group, in amounts proportional to the isocyanate groups formed, the preferred salts to use are amine hydrochlorides. However, the use of the free amines is preferred since it avoids the manufacture of the amine salts and since less of the volatile acids, for example hydrogen chloride, has to be separated from the reaction mixture.

The other starting material is phosgene. Since the phosgenation is carried out in the absence of organic solvents, the phosgene is preferably employed in excess, advantageously in such amounts that the reaction mixture contains at least 3, and preferably from 4 to 8, moles of phosgene per amino group of the organic amine.

The isocyanates are manufactured in a two-stage reaction.

In the first reaction stage, the starting materials, namely the primary amines and the phosgene, are mixed at from −30° to 60°C, preferably from 0° to 50°C, under atmospheric pressure or, preferably, superatmospheric pressure, in particular at pressures of from 14 to 55 bars or slightly above, whilst at the same time grinding the reaction mixture to an average particle size of from 1 to 100 $\mu$, preferably of from 1 to 50 $\mu$. The primary amine to be incorporated into the liquid phosgene is preferably in the form of a liquid, a melt or, where appropriate, a powder. Since the reaction between the primary amines and the phosgene takes place in the main at the surface of the particles if the reaction is carried out in a heterogeneous phase, it is necessary to mix the starting materials thoroughly and to grind the instantly produced reaction mixture of amine, carbamyl chloride and amine hydrochloride finely and as rapidly as possible, and to suspend it in phosgene, to prevent the formation of urea form carbamyl chloride and free, unconverted amine.

The mixing and simultaneous grinding are carried out in devices conventionally employed to grind, or enlarge the surface area, of solids and to manufacture suspensions of solids. Examples which may be mentioned are the Supraton machines (Deutsche Supraton, Dusseldorf, West Germany), Turrax equipment, (Janke & Kunkel KG, Staufen, West Germany) or Tornados (Emmendinger Maschinenfabrik GmbH, Emmendingen, West Germany). Grinding equipment wherein the grinding is carried out at energy densities of more than 5 kW/cubic meter of grinding volume, preferably of from about 10 to about 1,000 kW/cubic meter of grinding volume, are very suitable and are used preferentially. The mixing and grinding process is continued until all the primary amines have been converted to carbamyl chlorides and amine hydrochlorides. After a certain reaction time, the average particle size remains constant. The residence times for this stage of the reaction depend greatly on the activity of the amine used and on the efficiency of the mixing and grinding device and can vary from one second to 3 hours. However, it is preferred that residence times of from one second to 30 minutes should suffice to give quantitative conversion of the amine to carbamyl chloride and amine hydrochloride without detectable formation of by-products.

This stage of the reaction can be carried out continuously by using a mixing and grinding device in which the reaction mixture is recycled, for example a recycling grinding pump. At fairly high throughputs, it is preferred to connect several, for example from 2 to 15, and preferably from 2 to 10, mixing and grinding devices in series or, if appropriate, in parallel, and to feed amine/phosgene mixture to them individually or conjointly.

The amine-free suspension of carbamyl chloride and amine hydrochloride in phosgene, formed in the first stage, is fed to the second stage of the reaction.

In this second stage, the reaction of amine hydrochloride with phosgene to give carbamyl chloride, and its decomposition to give isocyanate and hydrogen chloride is carried out, preferably in a pressure vessel at from 100° to 180°C, preferably from 120° to 160°C. To ensure the presence of a liquid phosgene phase, the reaction mixture is decomposed under a pressure of from 1 to 55 bars, preferably from 21 to 41 bars.

The phosgenation of the amine hydrochloride and the decomposition of the carbamyl chloride can be carried out in conventional reaction vessels. Examples are pressure vessels equipped with columns and condensers, in which excess phosgene is condensed in a condenser and the reflux is fed to the reaction mixture whilst the hydrogen chloride eliminated is discharged continuously through the condenser. Preferably, the reaction is carried out in a column with a reboiler and top condenser; the reaction mixture is fed continuously to the column and the hydrogen chloride formed is discharged at the top of the column and the phosgene/isocyanate mixture at the bottom of the column. The phosgene/isocyanate mixture obtained can be fractionated, and purified, by distillation.

The monoisocyanates manufactured in accordance with the invention are valuable intermediates for the manufacture of dyes, plant protection agents, textile auxiliaries and paper auxiliaries. The diisocyanates and/or polyisocyanates are used, inter alia, to manufacture polyurethane plastics, for example rigid, semi-rigid and soft foams, elastomers, surface coatings, filaments, adhesives and films.

In the Examples, the parts are parts by weight.

EXAMPLE 1

50 g of a powdered mixture of 80 parts of 2,4-toluylenediamine and 20 parts of 2,6-toluylenediamine are introduced into 398 g of liquid phosgene at 0°C whilst thoroughly mixing, and grinding, the batch at an energy density of 300 kW/cubic meter of grinding volume with a Turrax TV 45 (Janke & Kunkel KG, Staufen/Brsg., West Germany). After a residence time of 30 minutes, the suspension formed is transferred into a 600 ml steel autoclave surmounted by a condenser. The autoclave is heated to 150°C whilst keeping the pressure at from 30 to 35 bars by releasing some of the continuously formed hydrogen chloride at the top of the condenser used to condense the phosgene. When the evolution of hydrogen chloride has ceased, the autoclave pressure is released, whereupon the excess phosgene distils off. The residual phosgene dissolved in the toluylenediisocyanate formed is removed by passing a stream of nitrogen through the mixture at 100°C. A distillation under reduced pressure, using a simple descending condenser, gives 61 g (85.5% of theory) of 99.9% pure toluylenediisocyanate mixture.

COMPARATIVE EXAMPLE 50 g of a mixture of powdered 2,4-toluylenediamine and 2,6-toluylenediamine in the weight ratio of 80 : 20 in 398 g of liquid phosgene are introduced, at 0°C, into a glass flask of 1,000 ml capacity. The reaction mixture is mixed thoroughly with a high speed paddle stirrer. After a residence time of 8 hours, the resulting suspension is transferred into a 600 ml steel autoclave surmounted by a condenser, and the reaction is completed at 150°C, analogously to Example 1. The yield of pure mixture of 2,4-toluylenediisocyanate and 2,6-toluylenediisocyanate is 55.9 g (78.2% of theory).

EXAMPLE 2

35 g of a powdered mixture of 2,4-toluylenediamine and 2,6-toluylenediamine in the weight ratio of 80 : 20 are introduced into 398 g of liquid phosgene at 0°C, whilst thoroughly mixing and grinding the batch at an energy density of 180 kW/cubic meter of grinding volume with a Tornade ET 20 (Emmendinger Maschinenbau GmbH, Emmendingen, West Germany). After a residence time of 15 minutes, the reaction mixture is transferred into the autoclave described in Example 1 and the reaction is continued at 150°C. The hydrogen chloride liberated is released in such amounts as to keep the pressure at from 30 to 35 bars. When the reaction has terminated, the mixture is worked up analogously to Example 1, giving 43.8 g (87.6% of theory) of a 99.9% pure toluylenediisocyanate mixture.

EXAMPLE 3

70 g of a powdered mixture of 2,4-toluylenediamine and 2,6-toluylenediamine in the weight ratio of 80 : 20 are introduced into 398 g liquid phosgene at 0°C whilst thoroughly mixing and grinding the batch at an energy density of 500 kW/cubic meter of grinding volume with a Turrax TV 45. After a residence time of 15 minutes, the suspension is heated in an autoclave to 170°C analogously to Example 1 and the hydrogen chloride liberated is released in such amounts as to keep the pressure at from 43 to 48 bars. On removing the excess phosgene and distilling the polyisocyanate, 86.2 g (86.2% of theory) of a mixture of 2,4-toluylenediisocyanate and 2,6-toluylenediisocyanate is obtained.

EXAMPLE 4

70 g of a melt of 2,4-toluylenediamine and 2,6-toluylenediamine, in the weight ratio of 80 : 20, which has been heated to 90°C are added dropwise to 398 g of liquid phosgene at 0°C, whilst mixing and grinding the batch at an energy density of 500 kW/cubic meter of grinding volume with a Turrax TV 45. After a residence time of 15 minutes, the reaction is completed as in Example 1. 83.7 g (83.7% of theory) of a mixture of 2,4-toluylenediisocyanate and 2,6-toluylenediisocyanate are obtained.

COMPARATIVE EXAMPLE

If a mixture of 2,4-toluylenediisocyanate and 2,6-toluylenediisocyanate is prepared analogously to Example 4 but using a high-speed paddle stirrer instead of a Turrax TV 45, the product is obtained in a yield of 74.3 g (74.3% of theory).

EXAMPLE 5

75 g of a polyphenyl-polymethylene-polyamine (about 0.76 equivalent of primary amino groups) melt are added dropwise to 400 g of liquid phosgene (4.08 moles) at 0°C, whilst mixing and grinding the batch at an energy density of 500 kW/cubic meter of grinding volume with a Turrax TV 45. After a residence time of 3 hours at from 0° to 5°C, the reaction is completed analogously to Example 1. After distilling off the excess phosgene in a stream of nitrogen at 160°C/5 mm Hg, a polyphenyl-polymethylene-polyisocyanate mixture containing 30.5% of free isocyanate groups and having a viscosity of 438 cst at 25°C is obtained in a yield of 84 g.

EXAMPLE 6

To a Supraton pump arranged in a brine-cooled residence loop and provided with an overflow leading to a pressure column there are fed, through a two-fluid nozzle, 1.2 kg/h of a melt at 110°C of a mixture of 2,4- and 2,6-toluylenediamine at the weight ratio 80 : 20 and 12 kg/h of liquid phosgene at a pressure of 35 bars. The mixture is ground and mixed at an energy density of 800 kW/cubic meter of grinding volume with a mean residence time of 20 minutes at 0°C. The suspension overflowing to the pressure column is decomposed at the same pressure of 35 bars and a temperature of 160°C. The pressure is maintained constant at 35 bars by releasing the continuously liberated hydrogen chloride at the top of the column. The excess phosgene is separated from the mixture discharged at the bottom and 1.6 kg/h (94% of theory) of a mixture of 2,4- and 2,6-toluylene diisocyanate isolated by vacuum distillation.

We claim:

1. A method of preparing organic isocyanates which comprises (a) mixing together in the absence of an organic solvent a primary amine with at least 3 moles of phosgene per amino group of said primary amine and simultaneously grinding the reaction mixture to an average particle size from about 1 to 100 $\mu$, and (b) heating the resulting suspension of carbamyl chloride and amine hydrochloride in presence of phosgene to a temperature of from about 100°C to about 180°C and at a pressure of from about 14 to 55 bars to form the corresponding isocyanate.

2. A process for the manufacture of organic isocyanates, as claimed in claim 1, wherein organic aliphatic, cycloaliphatic and aromatic diamines and/or polyamines are used as the primary amines.

3. A process for the manufacture of organic isocyanates as claimed in claim 2, wherein 2,4-toluylenediamine, 2,6-toluylenediamine, mixtures of 2,4-toluylenediamine and 2,6-toluylenediamine, 4,4'-, 2,4'- and 2,2'-diaminodiphenylmethane, mixtures of 4,4'-, 2,4'- and 2,2'-diaminodiphenylmethanes, 2,4,6-triaminotoluene, mixtures of polyphenyl-polymethylene-polyamines and mixtures of diamino-diphenylmethanes and polyphenyl-polymethane-polyamines are used as aromatic diamines and/or polyamines.

4. A process for the manufacture of organic isocyanates as claimed in claim 1, wherein the primary amines are reacted with from 4 to 8 moles of phosgene per amino group of the primary amine.

5. A process for the manufacture of organic isocyanates as claimed in claim 1, wherein the grinding of the reaction mixture is carried out at energy densities of from about 10 to about 1,000 kW/m³ of grinding volume.

* * * * *